United States Patent [19]

Dileo et al.

[11] Patent Number: 5,786,528
[45] Date of Patent: Jul. 28, 1998

[54] WATER INTRUSION TEST FOR FILTERS

[75] Inventors: Anthony J. Dileo, Westford; Richard W. Gray, Chestnut Hill, both of Mass.

[73] Assignee: Millipore Corporation, Bedford, Mass.

[21] Appl. No.: 711,755

[22] Filed: Sep. 10, 1996

[51] Int. Cl.$^6$ .................................................. G01N 15/08
[52] U.S. Cl. .................................................................. 73/38
[58] Field of Search ........................... 73/38, 40; 210/85, 210/87, 90

[56] References Cited

U.S. PATENT DOCUMENTS

| | | | |
|---|---|---|---|
| 5,353,630 | 10/1994 | Soda et al. | 73/38 |
| 5,594,161 | 1/1997 | Randhahn et al. | 73/38 |
| 5,616,828 | 4/1997 | Kuczenski | 73/38 |

*Primary Examiner*—Michael Brock
*Attorney, Agent, or Firm*—John Dana Hubbard; Timothy J. King; Paul J. Cook

[57] ABSTRACT

An improved water flow test for determining the integrity and/or pore size distribution of a porous filter is disclosed. The improvement involves the ability to determine and take into account the changes in filter structure due to filter compaction or creep resulting from compressive forces when pressure is applied to the surfaces of the filter. By proper characterization of the filter under test, the initial system volume and the volume change associated with pressurizing the filter can be accurately determined at all points in time during a test cycle. As a result, composite flowrate changes (i.e. the flow due to filter compaction/creep plus the flow due to liquid intrusion) can be evaluated to distinguish between various flow components to accurately determine the pore size of the filter being tested or a filter defect.

11 Claims, 7 Drawing Sheets

WATER INTRUSION TEST FOR FILTERS

BACKGROUND OF THE INVENTION

This invention relates generally to a method and apparatus for determining both the pore-size characteristics and integrity of filters, especially porous membranes and membrane filter devices. Specifically, this invention relates to a method and apparatus for determining the pore-size characteristics and/or integrity of a membrane or filter based upon liquid intrusion technology through the application, under pressure, of a liquid to the membrane which does not spontaneously wet the porous structure of the membrane.

Presently, the pore-size characterization and determination of integrity for membranes and filters, in general, are performed by various procedures, the most common of which are referred to as, among other things, "air-flow porosimetry", the "bubble-point test" or "bubble-point determination", and the "diffusion test". In addition, membranes, especially hydrophobic membranes, can also be characterized and tested by procedures commonly referred to as the "water intrusion-pressure determination" and the "water flow test" or "water intrusion test".

The bubble-point test and air-flow porosimetry utilize a liquid which spontaneously wets the membrane in question, and are based on the fact that subsequent attempts to displace the wetting liquid with a gas require that the gas pressure be elevated to some critical level dependent on the size of the pores, or the size of defects if present, in order to overcome the surface-tension forces holding the liquid in the pores. The equation for this critical pressure, defined as the bubble point pressure, is a variation of the Young-Laplace equation for capillary pressure drop, in this application often called the Washburn equation:

$$P_{BUBBLE\ POINT} = 4K\ \sigma \cos(\theta)/d \qquad \text{(Equation 1)}$$

where;

$P_{BUBBLE\ POINT}$ = bubble-point pressure
K = the pore perimeter (shape) correction factor
σ = surface tension of the liquid
θ = contact angle of the liquid against the solid
d = the diameter of the pore Equation 1 is rarely actually used to quantitatively calculate a pore size from empirical bubble-point data, since the pore perimeter correction factor, K, is rarely known independently. Instead, since the equation indicates that the bubble point is inversely related to the pore diameter, it is used to qualitatively rank the relative pore size of membranes according to their bubble-point pressures. Further, since particle retention efficiency is related to the pore size, Equation 1 also serves as a conceptual justification for empirically correlating the retention efficiency of membranes of various pore sizes to their bubble points. Membrane manufacturers have taken advantage of this retention—vs.—bubble point relationship to identify the critical bubble point required for a desired level of retention, and filter users conduct bubble point determinations to confirm that the filter in question is integral and of the appropriate pore size.

Air-flow porosimetry and a visual version of the bubble-point test for membrane samples are described by ASTM Method F316-86. In general, the bubble-point test is performed by pre-wetting the membrane with an appropriate liquid to be used and mounting the membrane in a specially designed holder which allows a visually observable layer of liquid to be placed on the downstream, i.e., upper side of the membrane. In the case of a bubble-point test of an enclosed filter, the filter is flushed with the liquid to wet the membrane. The pressure of air or other gas on the upstream side of the membrane is then increased, and the downstream liquid layer or the outlet from the enclosed filter is observed for the formation of continuous streams of bubbles. The pressure at which these bubbles first appear is called the visual bubble-point pressure of the sample. When testing hydrophobic filters or membranes, a solvent such as alcohol must be used to allow the surface to be wet in order to perform the bubble-point test. This solvent, which is toxic to most biological fluids, may be difficult to remove from the membrane and thus there are safety concerns associated with the use of such toxic solvents.

For relatively large filters, which experience significant diffusion rates at pressures below the bubble point, the visual bubble point pressure is difficult to identify accurately and a more analytical method is used to determine the bubble point pressure. In this case, the rate of flow of gas through the filter is measured as a function of the imposed gas pressure, and the pressure at which the flow makes a transition from relatively low flow rates, which are indicative of diffusion only, to significantly higher flow rates, which is indicative of bulk gas flow through pores or defects, is referred to as the bubble-point pressure of the filter.

In the diffusion test the gas flow rate through the wetted filter is measured after the filter is exposed to a constant upstream gas pressure equal to, or slightly below, the minimum bubble-point pressure required for the filter. Similar to a bubble-point test, the filter is pre-wet with an appropriate liquid. At a properly selected test pressure, the measured flow rate will be relatively low when the filter is integral and of the pore size. The source of gas flow through an integral filter at pressures below the actual bubble point of the filter is dissolution of gas into, diffusion through, and re-evaporation from the liquid filling the pores, without forcing the liquid out of the pores. In such a test, a filter with an undesirable large pore size or with a defect will exhibit relatively large gas flow rates as a result of the test pressure being in excess of the filter's actual bubble point.

Both the diffusion and bubble point integrity tests require the filter to be completely wetted with an appropriate fluid. The selection of the wetting fluid depends upon the filter material of construction. Typically, water is used as the wetting fluid in tests involving hydrophilic filters. Mixtures of alcohol/water are typically used to wet hydrophobic filter media. These alcohol/water mixtures present deficiencies that limit the routine application of integrity testing to hydrophobic filters. Alcohol solutions present a safety (explosion) hazard and are difficult to flush out of the filter after the test requiring large amounts of flush water. Alcohol integrity tests can be quite variable unless tightly controlled due to alcohol evaporation; which is especially true at temperatures between 25° and 30° C. Finally, alcohol/water integrity tests are typically conducted off line to avoid contamination of the downstream piping with alcohol.

An alternative technique which has achieved recent commercial success in assessing filter integrity is the water flow rate/intrusion pressure determination hereinafter referred to as the water flow test. This test which is particularly suitable for hydrophobic filters is conducted at a constant pressure and is similar to the diffusion flowrate determination with the exception that, in the water flow test, the filter or membrane is initially dry and the pressure at which water intrudes into and through the filter or membrane is noted. The intrusion pressure, which is a filter property analogous to the bubble-point pressure (Equation 1), is inversely related to the pore size and is, therefore, justifiably used to indicate the relative pore size of various membranes and can be correlated to determine retention efficiency. Thus, the intrusion pressure can be expressed by the following:

$$P_{INTRUSION} = -4K \sigma \cos(\theta)/d \qquad \text{(Equation 2)}$$

where the variables are the same as defined in Equation 1. Note that the negative sign results from the fact that the contact angle of water on a hydrophobic solid is greater than 90° and thus the cosine of this angle is negative.

There are two measurement techniques that are commercially used to determine the flowrates associated with filter testing involving each of the diffusion, bubble point and water flow tests, namely the pressure decay and the mass flow meter techniques. In the pressure decay technique the flowrate is determined by first exposing the filter to a constant pressure at or below the bubble point or intrusion pressure and subsequently isolating the filter from the pressure source and monitoring the pressure decay that will occur due to the diffusion or bulk flow (convection) of gas or liquid through the filter. Correlation of the measured pressure decay to the determination of an integral filter or of a pore size distribution is accomplished through application of the ideal gas law. In the mass flow technique the pressure applied to the filter is kept constant and the flowrate measured directly by means of a mass flow meter. The accuracy of the pressure decay technique is controlled by the ability to determine the size of the constant gas volume within which the pressure measurements are being made (typically the filter housing). This size determination is typically the first operation performed in the test procedure and the accuracy of subsequent flowrate determinations is dictated by the volume size determination. In the conventional mass flow technique, since the flowrate is determined directly, a volume determination is not required provided the temperature is ambient and stable. Under conditions where a mass flow measurement technique is applied to a test at elevated temperatures or if temperature variations occur during the test, a volume determination is required in this technique as well to assure accuracy. The accurate determination of the gas volume which is constant in both the bubble point and diffusion filter integrity test technique is a controlling limitation to the test accuracy.

In the case of integrity testing of hydrophobic filters using the water flow test technique, the upstream side of a dry hydrophobic filter is exposed to water at a constant pressure equal to, or slightly below, the minimum intrusion pressure required for the filter, and a measurement of the water flow rate into the filter housing is made. This measurement is inconveniently performed on the upstream side of the filter, either by measuring the flow of water directly with a flow meter, or by measuring the pressure as a function of time in an adjoining gas space and calculating the gas volume expansion rate, which just equals the water flow rate. The latter measurement is presently performed by automated testing devices. However, it is also possible to measure the downstream gas flow rate and equate this to the upstream water flow rate since the upstream water, membrane, and downstream air all move approximately together in a piston-like fashion at pressures below the intrusion pressure of the membrane. The same principles discussed above apply equally as well to hydrophilic filters except that a non-wetting liquid is used instead of water.

Unlike the diffusion test, the relatively low water flowrates observed in a water flow test conducted at a pressure below the normal water intrusion pressure are not due to gas diffusion. Instead, the water flow results from water flowing to fill the volume vacated by mechanical changes in the structure of the filter, as which can be the result of the shifting, compaction, and stretching of the filter when subjected to such pressure. These structural changes become exacerbated in a pleated membrane which is a structure common to many large-area filters. In an actual water flow test for pleated membrane cartridges, an observed low flowrate is predominantly indicative of pleat compaction only, and thus of an integral filter. On the other hand, a large flowrate is predominantly indicative of water flowing through undesirably large pores signifying a defect which is intruded at the test pressure.

The water flow test offers an important advantage for hydrophobic filters as compared to a bubble-point determination and diffusion test by eliminating the requirement of the use of a lowsurface-tension liquid, e.g. an alcohol or an alcohol-water mixture, to initially wet the hydrophobic filter. As previously mentioned, the use of such liquids pose safety and disposal problems that do not exist for the water flow test. The use of a water based test allows for filter integrity testing to be performed in-situ without special equipment such as hoods and the like. Also, such tests can be conducted immediately after steam sterilization at elevated temperatures.

As discussed above, the use of pressure decay or mass flow measurement techniques are also used in the water flow test. However, the use of these techniques in the water flow test requires the determination of the gas volume within the enclosed filter test volume under conditions in which the gas volume is continuously changing due to the cartridge pleat compaction. As a result, unlike the diffusion or bubble point case, the gas volume is not constant, but continuously increases as the filter cartridge is compacted. Therefore, the application of the water flow test at high accuracy is severely limited by the ability to account cumulatively for these continuous volume changes. Even after the gas volume determination is completed, the final segment of the integrity test protocol requires that the filter be brought to the test pressure and a final flowrate determination made. Continuously, throughout these steps, the cartridge continues to expand and/or change its mechanical structure and the volume of the enclosure in which the measurement is being made thus increases above that previously calculated during the gas volume determination phase of the test.

In fact, as published in "Membrane & Separation Technology News", January 1995, those skilled in the art have stated that the presence of interfering pleat compression effects prevents water flow testing from being useful in validating pleated cartridge filters. At the very least, inaccurate accounting or neglect of these volume changes with time can lead to significant errors in the determination of the waterflow rate, which could result in the interpretation of the pressure drop as a flowrate that is smaller than it actually is resulting in a false indication that a tested filter is within acceptable pore size limits when the filter actually is of greater pore size than its rated pore size or that the filter is integral when in fact it contains defects.

In spite of the above stated advantages of the water flow test, the effects of the continuous volume change associated with the compaction and creep or other structural change in the filter are a source of error, especially when testing small area filters or when rating small pore sizes filter devices. This is true when sizing small gas volume with either a pressure decay system or a mass flow measurement system, at non-ambient temperatures. Since the water flowrate being measured caused by this material compaction in these instances is so small at the lower end of the measurement range, it is difficult to differentiate it from the overall flow rate, i.e. the composite flowrate due to structural changes plus the flowrate attributed to liquid intrusion into and leaking from the pores. It is this latter flow which is used to establish the criteria for rating the pore size of the filter or for determining its integrity. As stated, the compaction complicates sizing efforts since the volume is constantly changing and this has led filter manufacturers that use the water flow test to heretofore set the "pass-fail" criteria level for filters being tested higher than required thereby lowering yields by improperly rejecting otherwise acceptable filters.

Therefore, it would be desirable to include as part of a water flow filter integrity test, a measurement technique which:

1. accurately determines the cumulative volume expansion of the filter structure under test, 2. determines this cumulative volume expansion independent of the test process control, 3. makes changes in the measured value more obvious as the imposed pressure is taken through the range over which the various sizes of pores are intruded, resulting in a more precise description of the relative pore-size distribution, and 4. makes, at a single pressure below the required intrusion pressure, the measured value for defective filter more obviously different from those for normal integral filters.

It is apparent that in order to take maximum advantage of the above mentioned water flow test so that it is more accurate than an alcohol based diffusion test, a dynamic analysis needs to be conducted that cumulatively determines the changing gas volume and the flowrate associated therewith over time as the filter is integrity tested. The determination of the cumulative dynamic volume expansion is necessary to extend the application of the water flow test to small area filters.

SUMMARY OF THE INVENTION

The present invention overcomes the disadvantages and limitations of the prior art by providing an improved technique for accurately testing the integrity or pore size distribution of a porous filter using liquid-intrusion and water flow measurement methods. The improved measurement technique rests on the ability to control and properly determine the changes in filter structure such as due to filter compaction or creep resulting from compressive forces when pressure is applied to the surfaces of the filter and to correlate the appropriate water flowrates to the integrity or pore size distribution of the filter being tested. The effect of these compressive forces on the filter has been known in the art for some time as has the resultant effect of producing a continuous liquid flowrate which can be significant enough to mask the presence of a defective filter during integrity testing. Despite the fact that this phenomenon has been known to those of skill in the art, there have not heretofore been reported any successful attempts to overcome this interference.

This invention is based on the discovery that all filters respond to applied pressure over time in an identical manner and that the change in filter structure is totally and immediately reversible with no significant hysteresis when the applied pressure is removed. Thus, the characteristic response of the change in volume associated with pressurization of a filter structure was found to be proportional to the applied pressure and a non-linear function of time and temperature. The characteristic response can be modeled by the following relationship.

$$V_c = [AP \text{ Log } (t+d) + BPt] * \exp(\alpha(T-RT)/RT) \quad \text{(Equation 3)}$$

where;

$V_c$ represents the change in volume of the filter structure resulting from application of intrusion pressure;

A, B and d are coefficients specific to the filter material type being tested representing the magnitude of the change in volume and are filter material and filter configuration dependent;

T is the temperature in °K;

RT is room temperature of 23 °K;

$\alpha$ is a constant reflecting the temperature dependence of the filter volume change;

P is the applied pressure (Psig); and t is the elapsed time from the application of pressure (min).

Using the relationship given in Equation 3, the volume change associated with pressurizing or depressurizing integral filters can be accurately and explicitly determined at all points in time during a test cycle. Using this relationship composite flowrate changes (i.e. the flow due to filter structure changes plus the flow due to liquid intrusion) can be properly evaluated and the component of flow associated with compression of the filter can be distinguished from the actual liquid flow resulting from intrusion into the pores of the filter to accurately determine the pore size of the filter being tested or a filter defect.

In accordance with a preferred embodiment involving the specific example of testing the integrity of pleated membrane filter cartridges, the test is divided into two phases, the first to determine the size of the gas volume within the test system on a continuous and cumulative basis, and the second to subject the cartridge to a test pressure, which is typically at or less than the intrusion pressure, to determine the pore size or integrity of the pleated membrane. Accounting for the change in volume due to pressure application and subsequent compaction of the pleats can be done using an expression of the type represented by Equation 3, with each of the four adjustable coefficients, which are characteristic of the filter cartridge material and configuration type as well as the test temperature, being determined by independent experiments. Including this expression explicitly in the ideal gas law equation accurately determines the gas volume at any pressure and time (i.e. the explicit determination). Alternatively, based on the aforementioned discovery and characterization of the response of the change in filter structure to applied pressure it was found that at times after initial pressure application (e.g. 15 seconds), the exponential term of Equation 3 could be approximated with a linear expression. Thus instead of determining the volume change associated with the cartridge through an independent experiment, one could use this linear approximation (including its unknown constant) in conjunction with the ideal gas law relationship and simultaneously determine both the unknown gas volume and the unknown constant during the gas volume sizing phase of the integrity test (i.e. the implicit determination). In the implicit determination, measurements of pressure decay values at two applied pressures below the intrusion pressure are needed to solve for the two unknowns.

Other aspects and advantages of the present invention will become apparent from the following detailed description taken in conjunction with the drawings.

DESCRIPTION OF PREFERRED EMBODIMENTS

Figure 1:
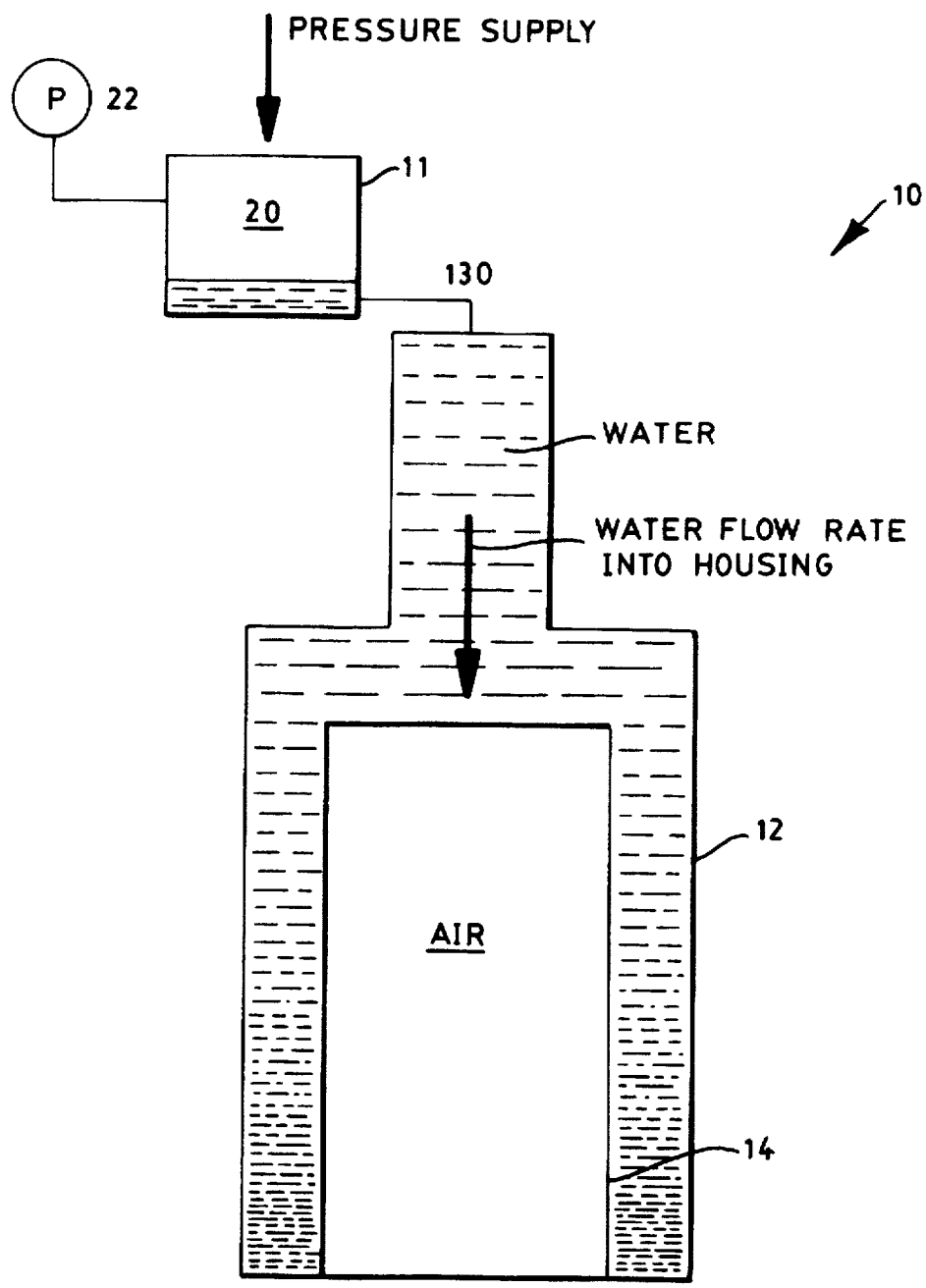
FIG. 1 is a schematic representation of a test stand for conducting water flow tests in accordance with the present invention.

FIG. 1 shows a system 10 for determining the integrity and/or pore size characteristics of porous membrane filter devices using water-intrusion pressure methods. The system includes a closed vessel 11 of known volume for holding water to be used as part of the water flow test. This vessel includes an air space 20 above the water which is connected to a pressure source (not shown). The vessel is connected to a test housing 12 by means of a conduit 13. Mounted within the housing is a porous pleated hydrophobic membrane filter cartridge 14 positioned so as to receive directly on the surface of the pleated membrane (not shown) water flowing from the vessel into the housing. Although in this embodiment the membrane filter cartridge is a hydrophobic pleated membrane cartridge, the principles of this invention extend to all types of membrane filters whether fabricated in devices or simply in sheet or tubular form. Also included within the operative scope of the present invention are polymeric microfiltration, ultrafiltration and reverse osmosis membrane filters as well as filters of these types made from other materials which undergo structural change under pressure and subsequent reversal without significant hysteresis when the applied pressure is removed. Further the principles disclosed herein apply equally to testing of hydrophilic membrane filters if a non-wetting fluid is used.

As configured, the pressurized water enters the test housing 12, is directed to the filter cartridge 14 and impinges upon all surfaces of the porous membrane fabricated within the cartridge. When exposed to the applied test pressure, the pleated cartridge structure will collapse increasing the volume within the cartridge filter due to pleat compaction. For a 10 inch long pleated cartridge, this volume change is approximately 36 milliliters. This large volume increase occurs in less than 30 seconds, typically in 15 seconds, and thereafter a change of about 0.1 ml/min continually occurs at an applied pressure of 38 psig. Water flows from the vessel 11 to fill this volume and the air space 20 increases accordingly. In the pressure decay measurement technique the pressurized closed vessel 11 is isolated from the applied pressure source. The expansion of the air space 20 due to pleat collapse will result in a drop in pressure which is detected by monitor 22, an accurate pressure transducer mounted on the walls of the vessel 11, and the measured pressure drop produces a water flowrate signal according to conventional techniques.

In accordance with an important aspect of the present invention, it has been discovered that all filter devices, regardless of material and configuration, respond to applied pressure in an identical manner and that the change in filter structure (which produces a change in volume) due to applied pressure is totally and immediately reversible without hysterisis when the applied pressure is removed. An example of the characteristic response representing this change in volume is provided in Equation 3 above. As seen, Equation 3 includes a set of four coefficients which pertain to the material of the filter, its configuration and the temperature of the test. For a pleated cartridge filter, the coefficient 'A' characterizes the volume associated with the immediate compaction of the pleats and depends upon the number of pleats, pleat height, cartridge length and temperature. The coefficient 'd' is the specific cartridge volume change after a predetermined time (e.g. 15 seconds) of exposure to pressure. The coefficient 'B' is predominantly the change in volume with time associated with material 'creep' into open regions of the filter support configuration and is related to the material, the support configuration and temperature. Finally, the coefficient "α" reflects the temperature dependence of the filter volume change. It should be noted that the specific definition of the coefficient 'd' will depend upon the exact mathematical relationship assumed to represent the response curve. With flat membrane filter devices, such as disc filters, only the coefficient 'B' is needed to adequately represent the response. The same is true of hollow fiber membranes provided they are rigid and do not balloon under applied pressure.

Independent Determination of the Characteristic Response

Figure 2:
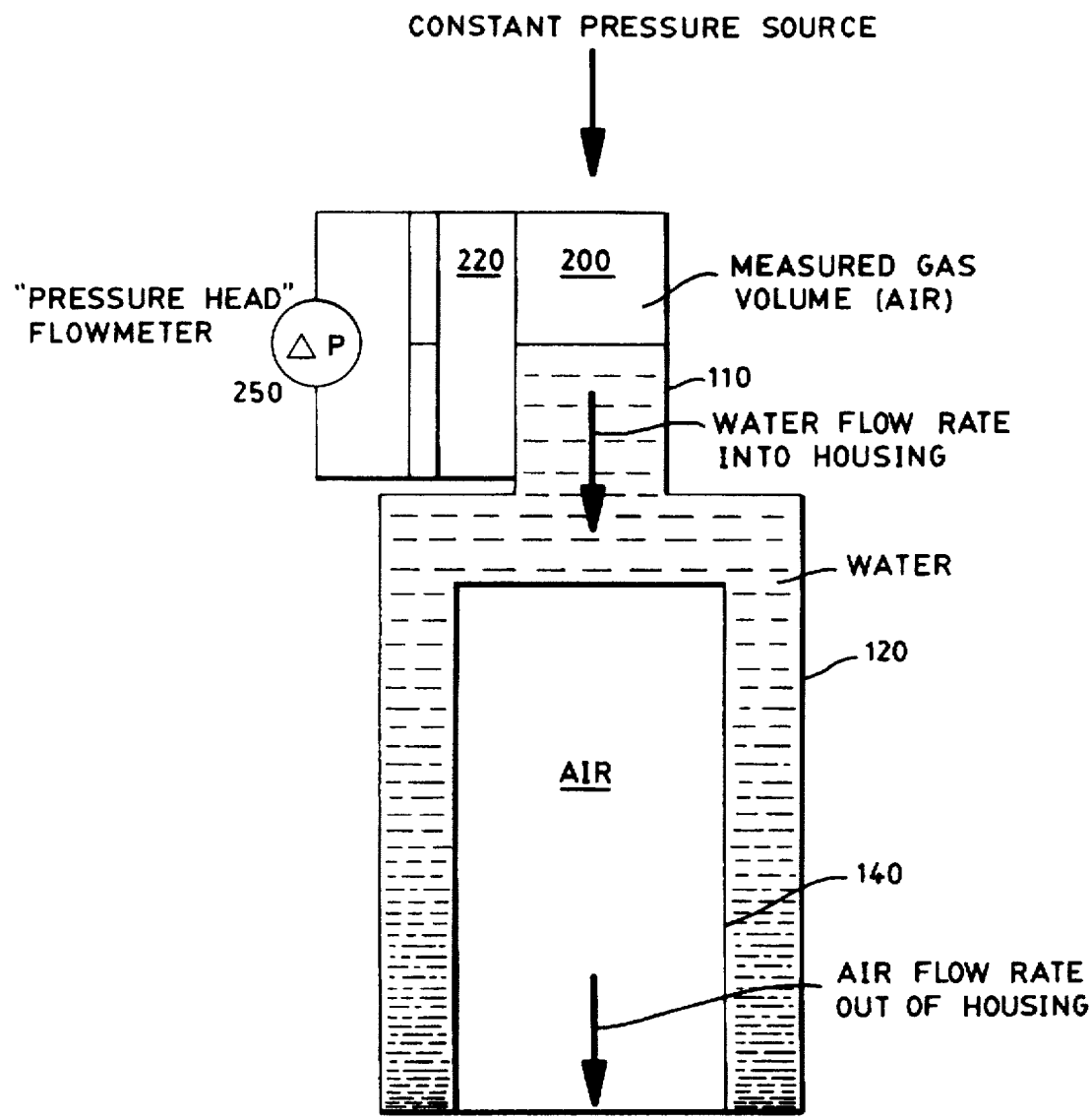
FIG. 2 is a schematic representation of a test stand for determining the characteristic response of volume changes of a filter to pressure in accordance with the present invention.
Figure 3:
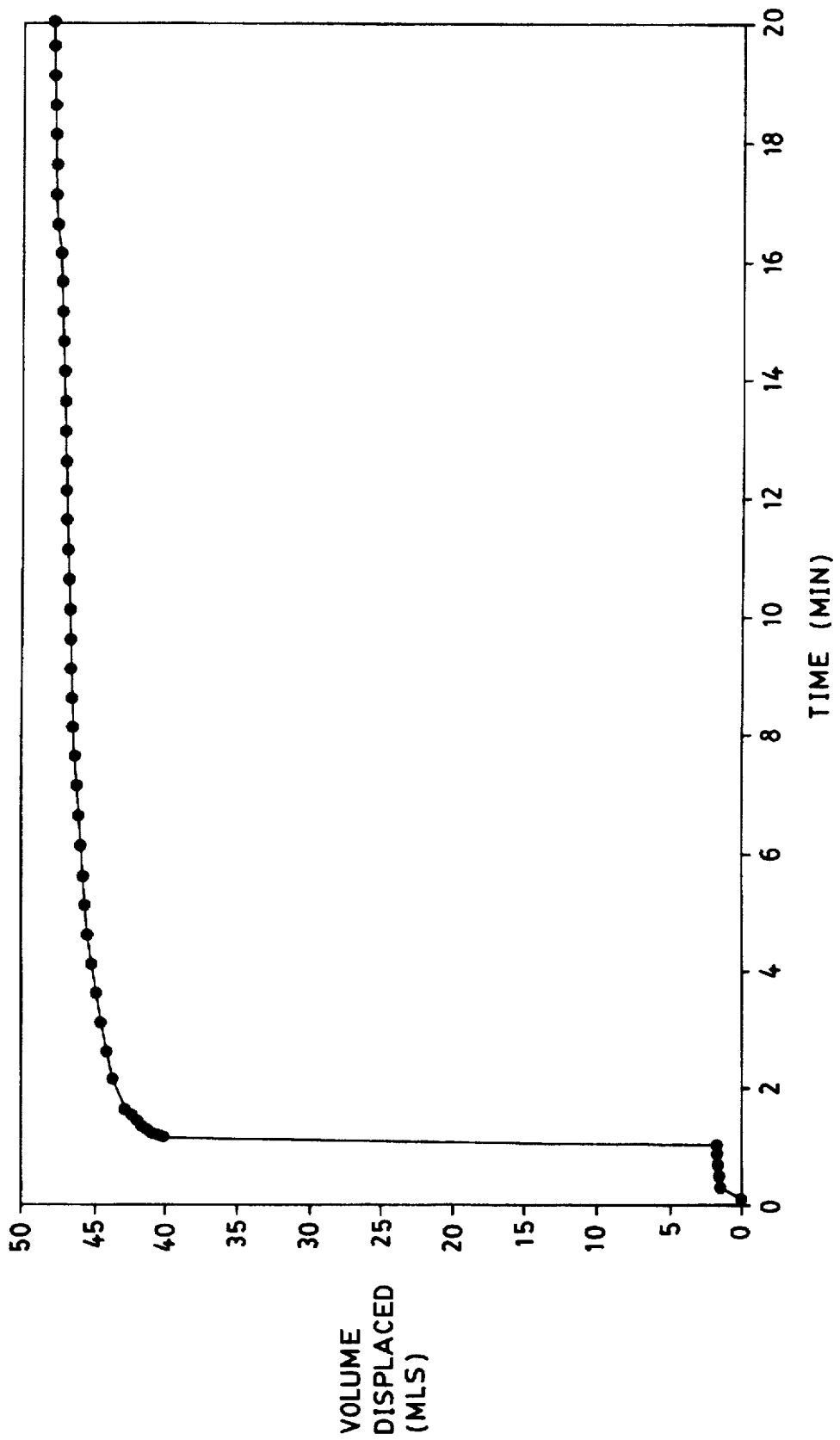
FIG. 3 is a graph showing the characteristic response of the change in volume of a hydrophobic pleated membrane filter cartridge over time under a constant applied pressure at constant temperature.

To be of use in the water flow test conducted in accordance with one embodiment of the invention involving the explicit determination, each of the coefficients, A, B and d, must be determined a priori by a set of independent experiments. To this end, the vessel 11 is no longer isolated from the pressure source, instead a constant pressure is continually applied to the filter cartridge 14. The system used to characterize the response is shown in FIG. 2 and includes a closed vessel 110 for holding water that includes an air space 200 above the water which is connected to a pressure source (not shown). The vessel is equipped with a liquid column site glass 220 for viewing the liquid level. Preferably, a pressure monitor 250 is also provided to determine the liquid level through a measure of head pressure. The vessel is connected to a housing 120 by means of a conduit 130. Mounted within the housing is a porous pleated membrane filter cartridge 140 positioned so as to receive directly on its surface water flowing from the vessel into the housing. As configured, the pressurized water enters the test housing, is directed to the filter cartridge 140 and impinges upon all surfaces of the membrane filter (not shown) fabricated within the cartridge. When exposed to the constant applied test pressure, the pleated cartridge structure will collapse increasing the volume within the filter cartridge. Water flows from the vessel 110 to fill this volume and the water level within the vessel 110 drops accordingly. The change in liquid level is measured directly to establish the volume change response dynamics. The measurement of the liquid can be measured by several methods. It can be determined visually using the site glass 220 attached to the vessel 110 or by the pressure monitor 250, an accurate differential pressure transducer for measuring the pressure between the air space 200 and the liquid level in the vessel 110. Alternately, a precise rotometer, or comparable liquid flow measuring device, can be included upstream of the housing 120 to measure the water flow associated with the response to the applied pressure. This characterization test is performed at a constant temperature and pressure and the change in liquid level is monitored as a function of time. Similar experiments can be performed as a function of pressure and temperature. These data can be then combined to determine the best values for 'A', 'B' and 'd' as well as $\alpha$ in Equation 3 that model this data set for each cartridge material type.

The values of the four coefficients required by Equation 3 are determined from the measured volume change response as follows. The value of 'd' is computed from the volume change after one minute of exposure to pressure. The value of 'A' is determined in a like manner after about 5 to 10 minutes. The value of the coefficient 'B' is determined by the slope of the nearly straight line at times greater than 10 minutes. The value of $\alpha$ is determined by setting the value of 'A' at different temperatures and reducing the values of 'B' and 'd' accordingly. Improved accuracy is obtained when the values of 'A' and 'B' are simultaneously determined through a conventional data fitting algorithm using techniques well known to those of ordinary skill in the art given that 'd' is defined at one minute.

The Air Space Sizing Step

The integrity test process is comprised of two distinct steps, a sizing step and a flowrate determination step. During the sizing step, the entire system 10 is first stabilized at a low pressure. After this stabilization, a known volume of gas at elevated pressure is added to the closed vessel 11 to raise the gas volume pressure to an intermediate value above the stabilization pressure but below the desired test pressure. Since the filter will rapidly undergo structural changes at this intermediate pressure a corresponding decay in pressure is measured. This pressure decay can be used to compute the size of the volume of the air space 20 as explained below. Subsequently, the entire system 10 is elevated to the test pressure and a pressure decay allowed to occur from this pressure from which the flowrate is determined. In prior water flow integrity tests, this pressure decay was used in combination with the volume computed in the previous step to determine the desired liquid flowrate. However, the process step of elevating the system 10 to the test pressure and the subsequent carrying out of the test consume a finite length of time, the duration of which results in a further volume expansion that is not included in the previous air space volume determination. Therefore, the flowrate that is computed using the artificially small volume will result in an incorrectly low flowrate allowing defective filter elements to appear 'good'.

It is a purpose of the present invention to accurately determine the volume of the air space 20 at the time and pressure of the test which step requires an accurate determination of the exact volume of the air space at the time of the flowrate determination. This is done by properly accounting for all of the volume changes that occur during the sizing step and during the time involved in setting up for the flowrate determination and adding these volume changes to the volume of the air space prior to the application of any pressure (referred to as the "initial volume") that is determined during the sizing step of the test procedure.

The Final Flowrate Determination

To be effective, a water flow integrity test performed with the pressure decay technique (or a mass flow technique under non-ambient or varying temperature conditions) requires that the volume of the air space 20 be accurately determined at the time of the test, a process often referred to as the sizing step. This step is done by first elevating the entire system 10 to an initial stabilization pressure, Ps, and subsequently introducing from an independent gas reservoir, of volume $V_T$, a known number of moles of gas at an elevated pressure, $P_T$, into the air space 20. The measured pressure response upon the introduction of gas can be used in conjunction with the ideal gas law to compute the volume of the air space 20. When the mass flow technique is used, the addition of the known number of moles is accomplished through the flow of gas for a defined time period and the measured pressure response is used as described herein.

As discussed above, the air space 20 is constantly expanding due to the compression of the filter element. Therefore, the volume of the air space computed from the introduction of gas at an elevated pressure will also include, in addition to the immediate cumulative volume change associated with the introduction of the stabilization pressure, an additional cumulative volume associated with the expansion of the filter at that pressure and time, i.e. when the computation is to be made. To accurately determine the air space volume at all times and pressures it is recognized that this volume is comprised of two volumes, one being the air space volume prior to the start of the test, i.e. the initial volume, and the other being the volume expansion associated with the filter, which for an integral filter is the known volume change resulting from the filter structural changes due to applied pressure. Therefore, in the sizing step the initial volume must be determined. To this volume the filter related volume expansion can be added at any time and pressure, for example, through the application of Equation 3 to accurately determine the volume of the air space 20 at the time of test. The air space sizing can be performed at a time shortly after the introduction of the known moles as described above through the use of the ideal gas law. The air space volume can be accurately determined from the pressure change measured at this time when the resulting pressure change is included in the ideal gas law calculation and incorporates the filter volume change effects ($V_c$) at three additional points in time. These effects are (expressed as the product of pressure and volume): 1) the change in the $P_1 * V_c$ product, where the volume $V_c$ is that associated with the cartridge compression that occurs at the pressure $P_1$ that exists in the system 10 just prior to the addition of the moles of gas into the air space 20 (which is at pressure $P_T$); 2) the change in the $P_2 * V_c$ product, where the volume $V_c$ is that associated with the cartridge compression that occurs at the pressure $P_2$ which is the equilibrium pressure that exists at the instant time of the introduction of the gas into the air space; and 3) the change in the $P_3 * V_c$ product, where the volume $V_c$ is that associated with the cartridge compression that occurs at the pressure $P_3$ at the time that the sizing computation is being performed. The pressures $P_1$, $P_2$ and $P_3$ can be directly measured and the values of $V_c$ calculated from the characteristic response of the filter being tested. Inclusion of these three additional factors allows for the sizing calculation to yield the initial volume of the air space 20. The exact volume of the air space 20 at the time of the flowrate determination at the test pressure can then be easily found by adding this computed initial volume of the air space to the cumulative volume attributed to the cartridge compression at the test pressure and test time determined from Equation 3.

Evaluation of the Volume Expansion Terms ($V_c$)

The three volume expansion correction terms discussed above can be determined by means of two approaches. The direct approach, i.e. the explicit determination, is through the direct application of Equation 3, once the coefficients 'A', 'B' and 'd' and α have been pre-determined. The $P_1*V_c$product can be determined directly through Equation 3 at that pressure and time. Alternately, the expression of Equation 3 can be linearized (for times greater than about 15 seconds after a pressure change) to an expression:

$$V_c \sim \Phi t \qquad \text{Equation 4}$$

where: Φ is a constant specific to the filter being tested. This linear procedure can be used without the independent determination of the coefficients 'A', 'B' and 'd'.

In this approach, i.e. the implicit determination, the value of the constant Φ and the initial volume of the air space 20 are simultaneously computed during the sizing step. If this approach is used, the test procedure is adapted to provide for the introduction of two gas injections of known moles each at a successively higher pressure but both below the intrusion pressure. The resultant volume and pressure changes are included in the ideal gas law computation evaluated at each of the two pressures to simultaneously determine both the initial volume of the air space 20 and the unknown constant Φ. As discussed above, the $P_i*V_c$ changes that exist just prior to the gas introductions, at the pressure immediately following the gas introduction, and at the time of the sizing computation need to be included in the computations involving the resultant pressure data.

The Final Flowrate Determination

Once the initial volume of the air space 20 is accurately determined using either the explicit or implicit determination, the test housing 12 is elevated in pressure to the test pressure. Under these conditions the cartridge will compress to equilibrate at that pressure and total elapsed time. The filter is then isolated from the pressure supply and the internal pressure allowed to decrease. The rate of filter expansion will drop accordingly and the cumulative volume will continue to change corresponding to the measured pressure decay. It is this flowrate that the test of the present invention is designed to determine. The flowrate determined at any point in time is computed from the measured pressure drop and the computed cumulative volume, which is the accumulated sum of the initial volume of the air space plus the cartridge compression volume at the pressure and time of the determination (including the further compression of the cartridge that occurs from the isolation of the filter to the point in time of the flowrate determination). Therefore, as long as the cumulative volume can be continuously determined an accurate flowrate can be computed from the measured pressure drop at any point in time.

Integral vs. Non-Integral Filters

In testing an integral filter, the cumulative volume should include the initial volume of the air space 20 in the vessel 11 plus the volume computed from the characteristic response of the filter cartridge 14 as discussed above. In testing a non-integral filter, the cumulative volume is the sum of the initial volume of the air space in the vessel plus the volume computed from the characteristic response of the filter plus the volume increase associated with the cumulative loss of liquid from the system through the leak (cumulative since the onset of pressurization at the beginning of the test). This additional volume change also contributes to the pressure changes measured during the sizing steps and needs to be included into the interpretation of the measured pressure to infer the air space 20 volume. These terms are included cumulatively as was the cartridge compression terms. Inclusion of these terms will result in the accurate computation of the initial volume of the air space 20. It should be noted that the loss of liquid through leaks does depend upon whether the applied pressure exceeds the intrusion pressure of the largest pores.

Similarly, volume changes accompanying filter structural changes as well as water convection are added to this computed initial volume in the determination of the final flowrate. By properly accounting for these independent effects following the guidelines set forth above, the contribution of the filter volume change can be separated from the contribution due to liquid flow through the filter pores defects.

Determination of Filter Integrity/Pore Size

The integrity or pore size of a filter is determined by comparing the computed flowrate of a 'test' filter to that of a pre-determined specification for integral filters of the type being tested. In all cases, the 'test' filter must be assumed to be non-integral and the pressure measurements interpreted as discussed above to include the cumulative effects of both the filter structural changes and the convective water loss. The specification (integrity or rated pore size) is obtained from the testing of a wide population of known integral filters in which the interpretation of the pressure decay data includes only the cumulative effects of the structural changes associated with that filter. The determination of known integral or rated pore size filters may be accomplished by challenging the filters with a known number and size of particles upstream of the filter and detecting the number of such particles downstream of the filter, as for example in bacteria challenge testing, or any other similar tests known to those of skill in the art.

TEMPERATURE EFFECTS

Due to variations in temperature that can occur during an integrity test, it is necessary in both the mass flow measurement technique as well as in the pressure decay technique to determine the initial volume of the air space 20 using the ideal gas law including terms explicitly accounting for temperature effects. The determination of the cumulative filter volume follows as described above with the addition that the characteristic response of the filter to pressure must be determined at the measured temperature. Therefore, the characteristic response modeled through Equation 3 should be evaluated at the temperature that exists in the air space 20 at each point in time. The temperature functionality is included in Equation 3 for this purpose.

EXAMPLES

Description of apparatus

Figure 7:
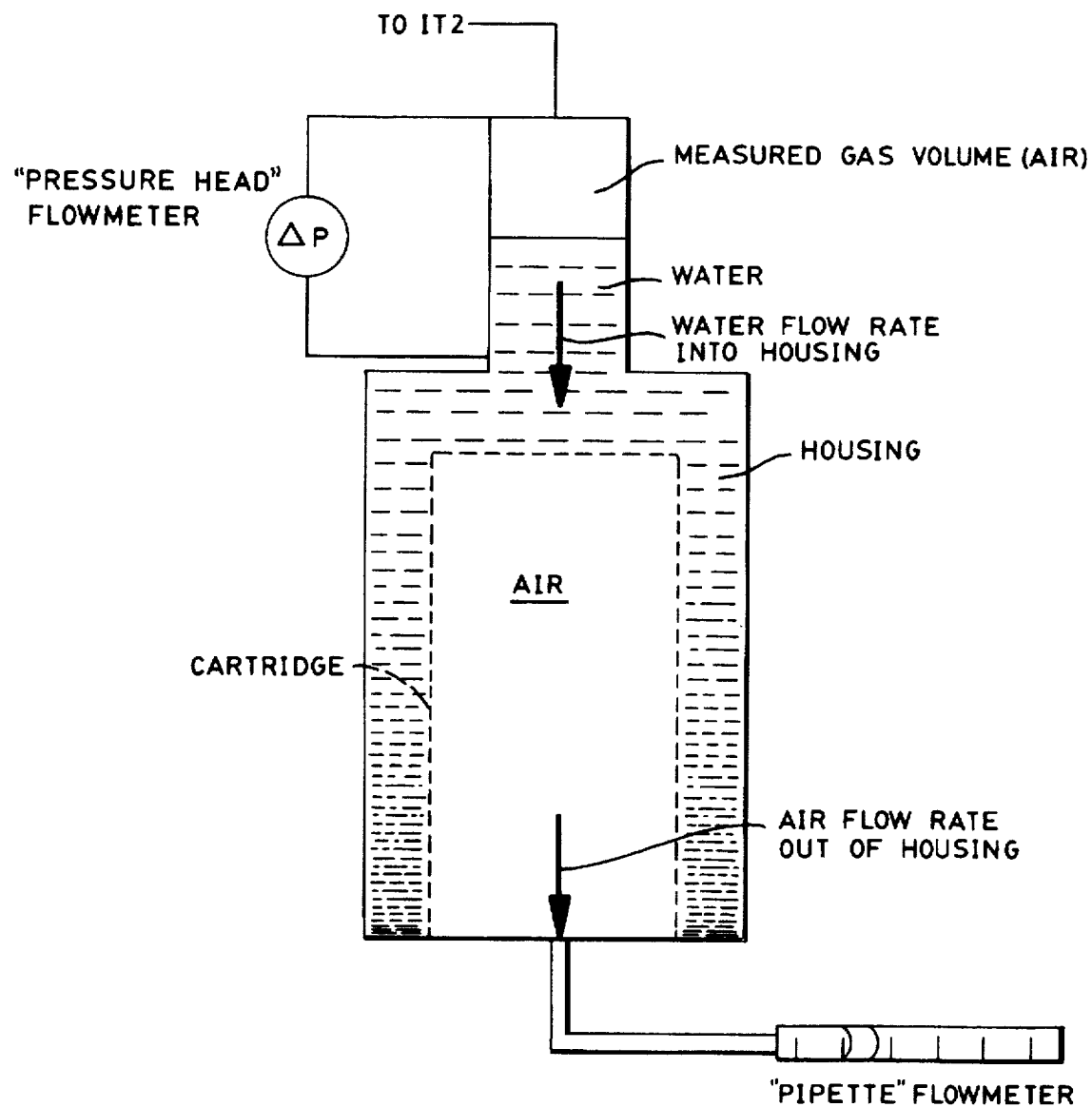
FIG. 7 is a schematic of the apparatus used to generate and measure volume and flowrate changes of simulated defective cartridge filters.

A filter housing and water reservoir as described above was equipped with a 'pressure-head' flow meter such that a calibrated 'reference' measurement could be made in parallel to the measurements made in accordance with the method of this invention for comparison purposes. This test apparatus is shown in FIG. 7. The 'pressure-head' flow meter consists of a column of water contained within an inlet pipe of known dimensions connecting the upstream side of the water-filled housing to a known and measurable gas volume. A calibrated differential pressure transducer was employed to measure the pressure difference between some point located below the air/water interface (located within the inlet pipe) and some point above the air/water interface. Using basic physical principles, this differential pressure reading can be converted to a volume of water with knowledge of the inlet tube inner diameter and water density. The instantaneous water flowrate can then be calculated by dividing the change in upstream water volume by the corresponding time duration. This flowrate was used as a reference value to which the computed flowrate can be compared for accuracy.

To simulate defective filters, artificial liquid leaks were established in parallel with the integral cartridge flow. Liquid leaks were purposely induced with the use of small-bore capillary tubes connected to the housing upstream of the filter. The volumetric flow rate through the tubes was determined by periodically collecting effluent samples from the capillary tubes and measuring and recording the duration and weight of the sample.

Example #1

Figure 4:
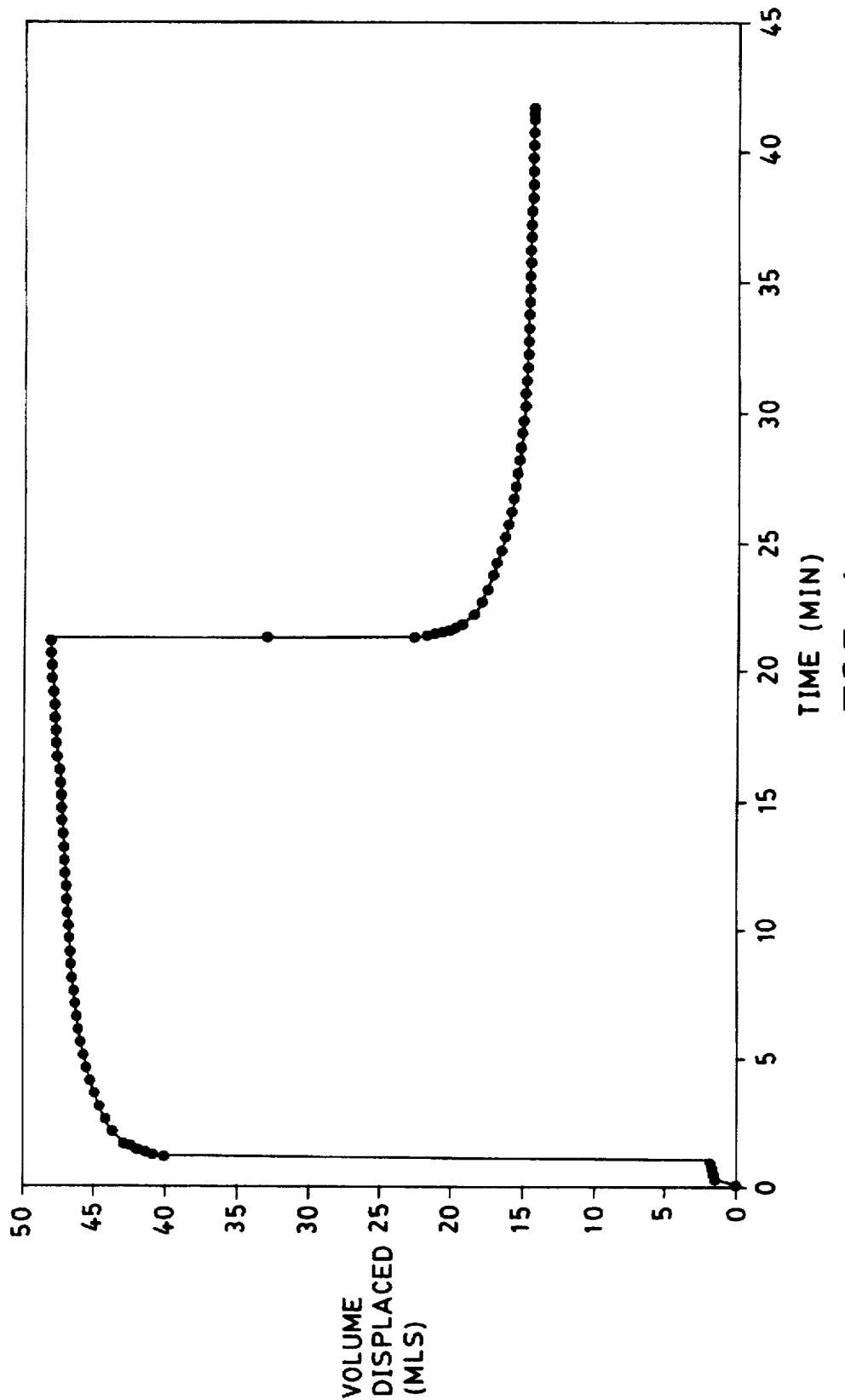
FIG. 4 is a graph showing the pressurization and depressurization of a membrane filter cartridge with membrane made of Teflon® polymer illustrating the rapid reversibility of the characteristic response of the changes in volume.

A single 10" Aervent™ pleated cartridge with Teflon® polymer membrane commercially available from Millipore Corporation, Bedford, Mass. was tested under 20 psi and the volume displaced as a function of time was monitored via the "pressure-head" flow meter. The volume displaced over 20 minutes is shown in FIG. 4. After 20 minutes under pressure, the pressure was removed (the applied pressure was returned to atmospheric pressure) and again the volume displacement was monitored. The test results are shown in FIG. 4.

Under pressure, the volume displaced increased very rapidly, within one-half minute approaching about 85% of the total displacement. The volume asymptotically approached the limiting value of 48 milliliters in the 20 minutes.

When the pressure was removed, the cartridge re-expanded following a function that was the mirror image of the one measured under pressure. No hysteresis was observed. However, the cartridge did not expand back to the starting volume. This is because the starting volume includes air that is trapped within the narrow confines of the pleats and cartridge assembly, which is displaced upon pressurization. Pressurization and depressurization was repeated between the 48 ml and 14 ml asymptotes of the FIG. 4 graph and the same effects observed.

Example #2

A series of experiments was conducted with pleated cartridge filters ranging in membrane area from 1.5 ft$^2$ to 20 ft$^2$ and ranging in size from a 5" long cartridge filter to three individual 10" pleated cartridges, both in capsule (plastic filter housing) form as well as within a stainless steel filter housing. Each pleated filter was tested individually to determine the flowrate of an integral filter and the flowrate with an artificially induced water leak to achieve a total water flow in excess of the specification of the filter.

The results were evaluated for accuracy of both the gas volume and the instantaneous flowrate derived from the methods of this invention and the conventional diffusion method that does not account for volume expansion changes. In addition, in those experiments in which an induced water leak was added, the measured volume should be the same as the cartridge in the absence of the leak. In addition, the measured instantaneous flowrate should be the sum of the integral cartridge flowrate determined in the first experiment plus the water leak flowrate. The accuracy of the two methods of interpretation was judged by their ability to compute a flowrate that equals the sum of the parts.

Figure 5:
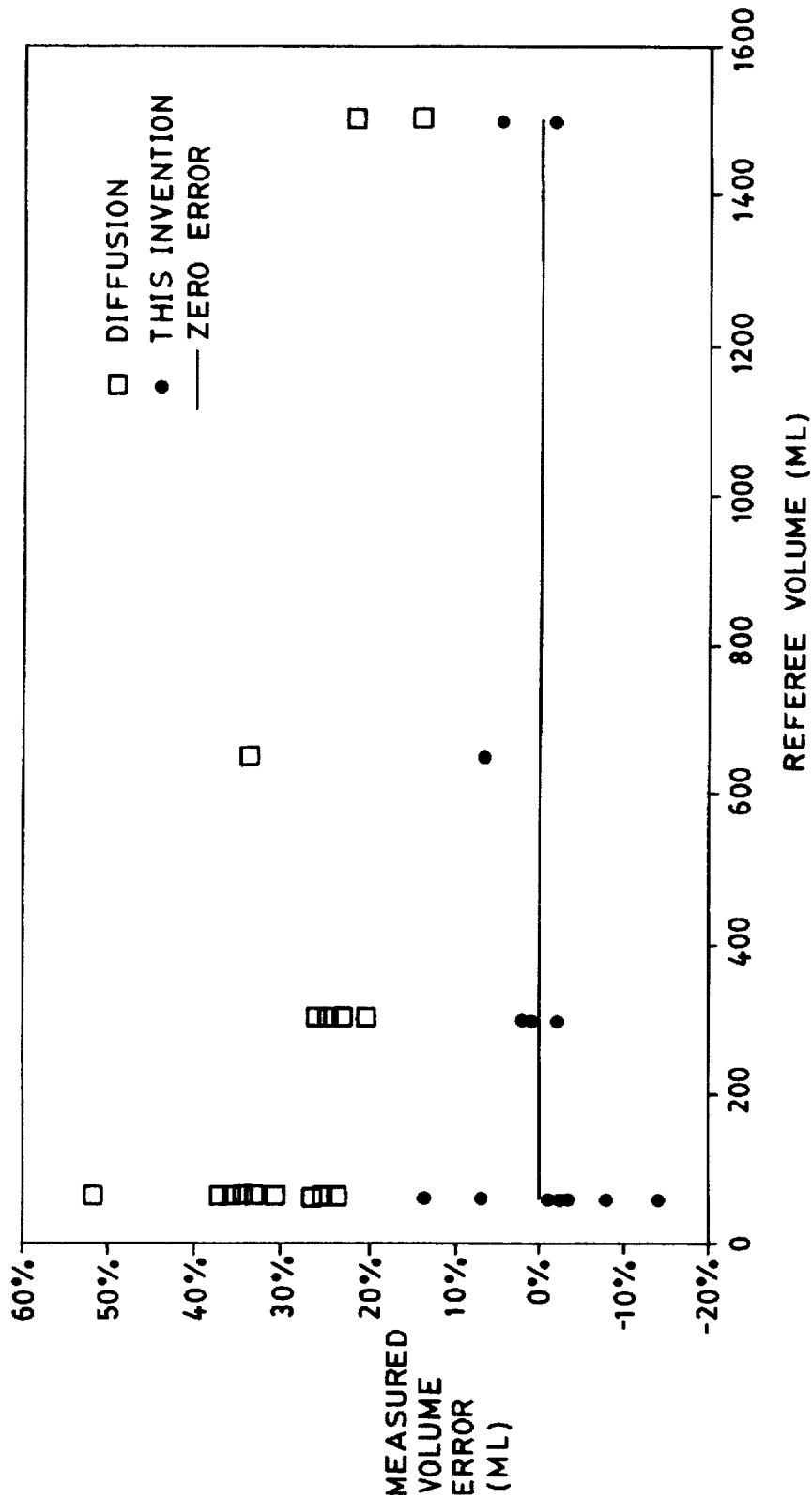
FIG. 5 is a graph comparing the error in the measured volume of a known reference volume in accordance with the present invention with the error in the measured volume of the known reference volume using conventional diffusional integrity test techniques.
Figure 6:
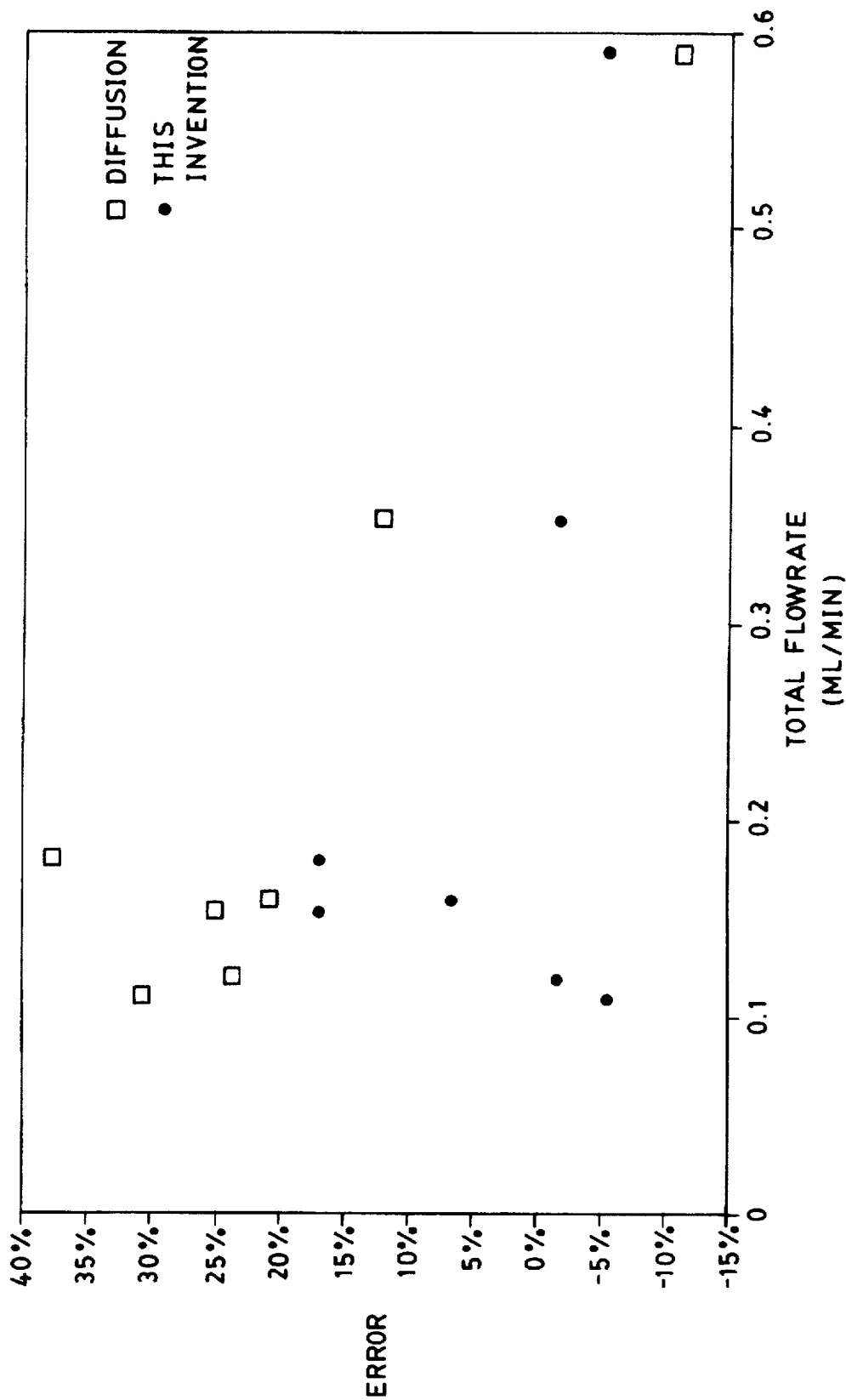
FIG. 6 is a graph comparing the error in the measured liquid flowrate of simulated defective cartridge filters with artificially imposed leaks in accordance with the present invention with the error in the liquid flowrate determined using conventional diffusional integrity test techniques.

The results of these tests are listed in Table 1. The error in the gas volume sizing using both methods is shown in FIG. 5, and the error between the measured flowrate and the sum of the integral cartridge plus the water leak rate for the simulated non-integral filter tests is shown in FIG. 6.

As can be seen, the errors obtained with the method of the present invention are significantly better across the entire set of test filters in the presence and absence of artificial water leaks than those computed without accounting for the volume changes associated with cartridge compression and water flowing through a simulated defect.

TABLE 1

| Cartridge Type | Reference Gas space Volume (ml) | Water leak flowrate added (ml/min) | Measured Referee Flowrate (ml/min) | Method of this invention | | Standard Diffusion | |
|---|---|---|---|---|---|---|---|
| | | | | Gas space Volume computed (ml) | Flowrate accounting for cartridge compression (ml/min) | Gas space volume without accounting for cartridge compression (ml) | Flowrate without accounting for cartridge compression (ml/min) |
| Aervent Opticap | 58 | — | 0.053 | 63.6 | 0.053 | 79 | 0.050 |
| Aervent Opticap | 58 | 0.1 | 0.14 | 58.7 | 0.127 | 73.9 | 0.115 |
| Aervent Optiseal | 58 | — | 0.06 | 58 | 0.065 | 75 | 0.060 |
| Aervent Optiseal | 58 | 0.1 | 0.149 | 58 | 0.149 | 75 | 0.127 |
| Durapore 5" cartridge | 58 | — | 0.07 | 58 | 0.062 | 90.2 | 0.045 |
| Durapore 5" cartridge | 58 | 0.11 | 0.12 | 57.6 | 0.149 | 90.4 | 0.112 |
| Durapore Opticap | 58 | — | 0.05 | 54.8 | 0.038 | 80 | 0.023 |
| Durapore Opticap | 58 | 0.06 | 0.09 | 51.1 | 0.116 | 77.8 | 0.076 |
| Durapore Optiseal | 58 | — | 0.046 | 67.7 | 0.046 | 81.2 | 0.025 |
| Durapore Optiseal | 58 | 0.07 | 0.11 | 67.7 | 0.121 | 80.3 | 0.091 |
| Aervent 10" | 300 | — | 0.18 | 293 | 0.171 | 362 | 0.201 |
| Aervent 10" | 300 | 0.58 | 0.74 | 301 | 0.765 | 369 | 0.768 |
| Durapore 10" | 300 | — | 0.122 | 305 | 0.122 | 374 | 0.143 |
| Durapore 10" | 300 | 0.23 | 0.33 | 305 | 0.358 | 376 | 0.310 |
| Aervent 30" cartridge | 650 | — | 0.66 | 694 | 0.62 | 868 | 0.68 |

TABLE 1-continued

| | | | Method of this invention | | Standard Diffusion | |
| | | | | | Gas space | Flowrate |
| Cartridge Type | Reference Gas space Volume (ml) | Water leak flowrate added (ml/min) | Measured Referee Flowrate (ml/min) | Gas space Volume computed (ml) | Flowrate accounting for cartridge compression (ml/min) | volume without accounting for cartridge compression (ml) | without accounting for cartridge compression (ml/min) |
| --- | --- | --- | --- | --- | --- | --- | --- |
| Aervent 30" cartridge | 650 | 4.54 | 5.13 | 694 | 5.14 | 868 | 5.13 |
| Durapore 3 × 10" cartridges | 1500 | — | 0.31 | 1475 | 0.333 | 1713 | 0.438 |
| Durapore 3 × 10" cartridges | 1500 | 0.28 | 0.61 | 1574 | 0.619 | 1828 | 0.655 |

*All cartridge filters are commercially available from Millipore Corporation

We claim:

1. A method for determining the integrity and/or pore size distribution of a porous filter by water intrusion flow testing which comprises:

positioning said filter in a test cell, introducing into said test cell a liquid a liquid which does not instantaneously filter into said test cell, the volume of said liquid being sufficient to surround said filter;

providing an enclosed gas space in fluid communication with said liquid, the combination of the volume of said gas space, the volume of said liquid surrounding said filter device and the volume of liquid within said filter device defining a system volume;

applying a pressure through said gas space to produce a composite liquid flowrate in said test cell consisting of a first flow component representative of a change in volume of said filter due to structural changes of said filter resulting form the compressive effects of applied pressure and a second flow component representative of liquid intrusion into and leaking from the pores of said filter;

calculating the cumulative volume of said gas space while pressure is applied to said filter to derive a value of said system volume at any time while pressure is applied;

determining an adjusted composite liquid flowrate measurement from said derived value of said system volume which is essentially solely indicative of said second flow component; and correlating said adjusted composite liquid flowrate with a pre-determined flowrate value indicative of known integral and/or rated pore size filters whereby the integrity and/or pore size distribution of said filter under test may be accurately determined.

2. The method of claim 1 wherein the cumulative gas volume is calculated by combining a predetermined characteristic response of the change in volume of said filter as a function of pressure, temperature and time with a determination of the initial volume of said gas space prior to applying pressure thereto.

3. The method of claim 2 wherein said characteristic response is determined a priori by applying a constant pressure source at constant temperature to said test cell and monitoring over time the change in volume of said filter.

4. The method of claim 2 wherein said initial volume of said gas space is determined by measuring the pressure changes resulting from adding a known gas volume at elevated pressure to said gas space and computing the corresponding volume change resulting from said added known gas volume and subtracting a second smaller cumulative gas volume at the time of said computing step, said second volume being determined in accordance with said characteristic response, to arrive at said initial volume.

5. The method of claim 2 wherein said initial volume of said gas space is determined by measuring the pressure changes resulting from the addition of a known mass of gas to said gas space and computing the corresponding volume change resulting from said added known mass of gas and subtracting a second smaller cumulative gas volume at the time of said computing step, said second volume being determined in accordance with said characteristic response, to arrive at said initial volume.

6. The method of claim 2 wherein said adjusted flowrate is determined by the product of a measured pressure change from applying pressure at the time an integrity and/or pore size distribution test isconducted and the cumulative gas volume calculated at that point in time.

7. The method of claim 1 wherein the cumulative gas volume is calculated by combining a linear characteristic response of the change in volume of said filter which includes a linear response constant and a function of time with a measure of the initial volume of said gas space prior to applying pressure thereto.

8. The method of claim 7 wherein said initial volume of said gas space is determined by measuring pressure changes resulting from the adding known gas volumes at elevated pressure to said gas space while simultaneously determining said linear response characteristic.

9. The method of claim 8 wherein said initial volume of said gas space is determined by measuring the pressure change in said test cell after a predetermined period of time after adding a known gas volume at an elevated first pressure followed by the step of measuring the pressure change after a predetermined period of time after adding a second known gas volume at an elevated second pressure greater than said first pressure and combining each of said measured pressure changes to determine said cumulative gas volume and said linear response characteristic.

10. The method of claim 7 wherein said initial volume of said gas space is determined by measuring the pressure changes resulting from adding a known mass of gas to said gas space while simultaneously determining said linear response characteristic.

11. The method of claim 7 wherein said adjusted flowrate is determined by the product of a measured pressure change from applying pressure at the time an integrity and/or pore size distribution test is conducted and the cumulative gas volume calculated at that point in time.

* * * * *